US010690607B2

(12) United States Patent
Monnier et al.

(10) Patent No.: US 10,690,607 B2
(45) Date of Patent: Jun. 23, 2020

(54) SAMPLE HOLDER AND LOCK-IN THERMOGRAPHY SYSTEM WITH SUCH

(71) Applicant: ADOLPHE MERKLE INSTITUTE, UNIVERSITY OF FRIBOURG, Fribourg (CH)

(72) Inventors: Christophe A. Monnier, Bottmingen (CH); Mathias Bonmarin, Zürich (CH); Federica Crippa, Fribourg (CH); Alke Fink, Düdingen (CH); Christoph Geers, Fribourg (CH)

(73) Assignee: NANOLOCKIN GMBH, Fribourg (CH)

( * ) Notice: Subject to any disclaimer, the term of this patent is extended or adjusted under 35 U.S.C. 154(b) by 65 days.

(21) Appl. No.: 16/098,285

(22) PCT Filed: May 2, 2017

(86) PCT No.: PCT/EP2017/060412
§ 371 (c)(1),
(2) Date: Nov. 1, 2018

(87) PCT Pub. No.: WO2017/191129
PCT Pub. Date: Nov. 9, 2017

(65) Prior Publication Data
US 2019/0154602 A1 May 23, 2019

Related U.S. Application Data (60) Provisional application No. 62/331,017, filed on May 3, 2016.

(51) Int. Cl.
*G01N 25/72* (2006.01)
*B01L 3/00* (2006.01)
(Continued)

(52) U.S. Cl.
CPC .......... *G01N 25/72* (2013.01); *B01L 3/50851* (2013.01); *C12M 23/12* (2013.01);
(Continued)

(58) Field of Classification Search
CPC ... A61K 38/00; B01J 19/0046; G01N 25/005; G01N 25/00; G01N 15/08; G01N 15/11;
(Continued)

(56) References Cited

U.S. PATENT DOCUMENTS

2013/0273648 A1  10/2013 Dorge et al.
2019/0025211 A1* 1/2019 Nakamura ............. C09K 11/06

OTHER PUBLICATIONS

I. Andreu et al., Accuracy of available methods for quantifying the heat power generation of nanoparticles for magnetic hyperthermia, International Journal of Hyperthermia, 29:8, 2013, pp. 739-751.
(Continued)

*Primary Examiner* — Don K Wong
(74) *Attorney, Agent, or Firm* — Hudak, Shunk & Farine Co. LPA (57) ABSTRACT

A sample holder for magnetic nanoparticle samples including a plurality of sample wells for holding a magnetic nanoparticle sample, which are distributed on a top surface of the sample holder. The sample wells are distributed such that a first distance between neighboring samples wells and/or a second distance between each peripheral sample well and a respective edge of the top surface of the sample holder and/or a third distance between a deepest point of the sample wells and a bottom of the sample holder is between 1 and 100 times greater than a thermal diffusion length of the sample holder material. The sample holder is used in a lock-in thermography system.

20 Claims, 5 Drawing Sheets

(51) Int. Cl.
*C12M 1/32* (2006.01)
*G01N 25/20* (2006.01)
*G01J 5/02* (2006.01)
*B82Y 15/00* (2011.01)
*G01J 5/00* (2006.01)

(52) U.S. Cl.
CPC ............ *G01J 5/0255* (2013.01); *G01N 25/20* (2013.01); *B01L 2200/0668* (2013.01); *B01L 2300/0819* (2013.01); *B01L 2300/123* (2013.01); *B01L 2300/168* (2013.01); *B82Y 15/00* (2013.01); *G01J 2005/0081* (2013.01)

(58) Field of Classification Search
CPC ..... G01N 15/10; B01L 3/5085; B01L 5/5085; B01L 3/50851; C12M 23/12; G01J 5/0255
See application file for complete search history.

(56) References Cited

OTHER PUBLICATIONS

Anoymous, Susse Labortechnik—Produktakatalog 2012/2013, 2012,p. 5, XP055389319, Retrieved from the Internet: URL:http://www.suesse.de/fileadmin/suesse/pdf/Katalog/Katalog Suesse_2012-2013.pdf.

J.C. Krapez, Compared performances of four algorithms used for digital lock-in thermography, QIRT'98 Quantitative Infrared Thermography 4,1998, Lodz, Poland, 8 pages.

Kim et al., Measurement of thermal properties of magnetic nanoparticles using infrared thermal microscopy, Infrared Physics & Technology, 57, Dec. 29, 2012, pp. 76-80, XP055389069.

Junyan et al., Research on thermal wave processing of lock-in thermography based on analyzing image sequences for NDT, Infrared Physics & Technology 53, 2010, pp. 348-357.

Gupta et al., Temperature Drift Correction for Fast Lock-in Infrared Thermography, 21st European Photovoltaic Solar Energy Conference, Sep. 4-8, 2006, Dresden, Germany, pp. 332-335.

Muller et al., Infrared Camera Based Thermometry for Quality Assurance of Superficial Hyperthermia Applicators, Institute of Physics and Engineering in Medicine, Physics in Medicine & Biology, 61, 2016, pp. 2646-2664.

J. Bante-Guerra et al., Infrared thermography analysis of thermal diffusion induced by RF magnetic field on agar phantoms loaded with magnetic nanoparticles, SPIE-International Society for Optical Engineering, Proceedings, vol. 8584, Feb. 14, 2013, p. 858412, XP055388848.

Breitenstein et al., Lock-in Thermography, Basics and Use for Evaluating Electronic Devices and Materials, Second Edition, Springer Series in Advanced Microelectronics, 2010, 261 pages.

* cited by examiner

SAMPLE HOLDER AND LOCK-IN THERMOGRAPHY SYSTEM WITH SUCH

FIELD OF THE INVENTION

The invention resides in the field of lock-in thermography and relates to a sample holder for holding magnetic nanoparticle samples, to a lock-in thermography system with such a sample holder and to a method for examining thermal radiation signals of magnetic nanoparticle samples by means of the lock-in thermography system, according to the independent claims.

BACKGROUND OF THE INVENTION

Lock-in thermography (LIT) is a known method for examining internal structures of objects by applying periodic energy waves and analyzing the resulting temperature profile of the area to be examined. Generally, when the input wave penetrates an object's surface, the wave is partially reflected in regions where the tissue to be examined is non-homogenous. The reflected wave interferes with the input wave and creates interference patterns in the local surface temperature of the object. Analysis of these interference patterns makes it possible to identify the internal structure of said object. LIT may e.g. be used for characterizing tissue in-vivo and detect skin lesions like for example regions with cancerous cells, such that identification of such tumors or malign cells, e.g. in case of skin cancer, can be performed without having to extract samples from the tissue.

With respect to this type of application it has been discovered that usage of nanoparticles in detection, characterization and potentially destruction of cancerous tumors is a very promising path in this field, particularly in view of the potential possibility of destroying tumors by non-invasive techniques.

Nanoparticles, i.e. materials at nanoscale with typical sizes of 1 to 100 nm in at least one dimension, offer a variety of unique properties. The capability of producing heat when exposed to an alternating magnetic field (AMF) is an extraordinary property of magnetic nanoparticles (MNPs). Due to the thermal energy, which is produced by MNPs when they are exposed to an AMF, they can be used for cancer therapy in a process generally known as magnetic hyperthermia. Efficient heating depends on different variables including magnetic field strength or frequency and chemistry, size and surface of the used MNPs. In order to choose the most efficient MNPs to be used at lowest possible concentration for magnetic hyperthermia treatment, this heating efficiency must be determined. The synthesis of typically used MNPs (mostly superparamagnetic iron oxide nanoparticles) is well described in the literature and different sizes and surfaces of these particles are commercially available (e.g. Chemicell, Advanced Magnetics, Nanocomposix).

The most commonly used factor to quantitatively reflect the heating power of iron oxide nanoparticles is the Specific Absorption Rate (SAR) in $W \cdot g^{-1}$, which is defined as the rate at which electromagnetic energy from a defined amount of magnetic material is absorbed by a unit mass of a material $$SAR = \frac{P}{m_{NP}}$$

where P is the heat power dissipated by the magnetic nanoparticles and $m_{NP}$ is the total mass of magnetic material. However, it must be noted that the SAR-value does not cover all variables; as mentioned above, the heating power is also depending on external factors like the magnetic field strength and frequency, making a further normalization step necessary. In this context, it has been shown that, at low frequencies and field strengths (i.e. which are mostly used in clinical settings), the SAR can be considered as a function of the frequency and square of the magnetic field. Consequently, the SAR can be further normalized in accordance with these assumptions. This value is referred to as the Intrinsic Loss of Power (ILP) in $nH \cdot m^2 \cdot kg^{-1}$ a system-independent parameter which is defined as:

$$ILP = \frac{SAR}{H^2 f}$$

where H is the strength of the AMF and f its frequency. The ILP is particularly useful in comparing results obtained by different experimental settings, batches and research groups. However, it should be kept in mind that this value represents only an approximation and only applies to a narrow experimental window.

The publication "Accuracy of available methods for quantifying the heat power generation of nanoparticles for magnetic hyperthermia" by I. Andreu and E. Natividad, Int. J. Hyperthermia, 29:8, 739-751 reviews currently available methods of SAR-determination of MNPs. In the paper, the conclusion is drawn that the determination of the heat efficiency of MNPs via thermal imaging requires a set up providing quasi-adiabatic conditions, i.e. the measured sample has to be thermally insulated in combination with the measurement conditions.

Standard calorimetric methods (e.g. fiberoptic cables or thermocouples) are the currently used approaches to evaluate the heating capabilities. However, they only provide measurement data from single one-dimensional points, and are consequently very limited in regard to reproducibility (in regard to sensor positioning), accuracy and precision. Although the set-up is easy to install, the correct fitting of the obtained data is challenging and the measurements are time consuming and invasive. Additionally, due to convection or conduction, the heat loss during measurements is not taken into account.

Beside the already mentioned applications, LIT is currently a standard method used for testing composite materials and electronic components (e.g. solar panels) and is based on the modulation of the thermal radiation. In short, the heat-generating stimulus (in this case, the AMF) is periodically modulated over a specified amount of cycles while an infrared camera continuously records the thermal events. The data acquisition and output differ from the other methods in that rather than recording variations of temperature over time the amplitude or the magnitude of the temperature oscillations during the modulation cycles is determined.

Generally, usage of nanoparticles in LIT gives rise to problems involving a number of factors like experimental set-ups and measurement conditions. Furthermore, commercially available MNPs show non-negligible batch to batch variations with respect to magnetic behavior, size distribution, crystallinity or surface.

Thus, due to the variations of the physical MNP-properties resulting from the manufacturing process, a pre-characterization of MNPs in terms of measuring heat production of magnetic nanoparticles in an alternating magnetic field before their usage in the actual application is very important for achieving good results with respect to the specific application.

SUMMARY OF THE INVENTION

It is therefore an objective of the present invention to improve the precision, accuracy and reproducibility of pre-characterization of MNPs with respect to said disadvantages.

In a first aspect of the invention this objective is solved by a sample holder for holding a plurality of magnetic nanoparticle samples and for usage in a lock-in thermography system. The sample holder comprises a plurality of sample wells distributed on a top surface of the sample holder. Each of the sample wells is adapted to hold a magnetic nanoparticle sample consisting of a plurality of magnetic nanoparticles embedded in a medium. The sample wells are distributed on the top surface such that a first distance between neighboring samples wells and/or a second distance between each peripheral sample well and a respective edge of the top surface of the sample holder and/or a third distance between a deepest point of the sample wells and a bottom of the sample holder is between 1 and 100 times greater than a thermal diffusion length of the sample holder material.

By dimensioning at least one of said three distances within the above range it is possible to manufacture a sample holder which is very suitable for usage in systems for characterizing MNPs as its own influence on measurements is minimized. Therefore, a characterization of the thermal properties of the nanoparticle samples can be carried out in a more accurate way. Whether only one of said distances or a combination of them is chosen to meet the above criterion depends on system setup. E.g. it may be helpful if the first distance fulfils the above criterion if e.g. all sample wells are filled with samples. The second distance may e.g. be chosen to meet the above criterion if the setup includes samples arranged in peripheral sample wells.

It is however preferred, although not necessary for improving measurement results, that the first, second and third distance all fulfil the above criterion in order to have the highest possible freedom degree in arranging samples in the sample holder and achieving a minimum influence of the sample holder on measurements.

Particularly, it is preferred that the first and/or the second and/or the third distance is/are at least 10 times greater than a thermal diffusion length of the sample holder material. Alternatively, or additionally, it is preferred that the first distance and the second distance and the third distance are equal. In this way the material amount used for building the sample holder can be optimized. If the first and/or the second and/or the third distance is/are substantially greater than a thermal diffusion length of the sample holder material, the sample can be considered placed in a thermally thick sample holder and thermally isolated. This configuration is optimal to calculate the SAR from the amplitude image and/or values.

In embodiments, the sample holder consists of a sample holder material which is opaque to infrared thermal radiation. This measure ensures that infrared thermal radiations are not transmitted by the sample holder material, such that potential losses by radiation through the sample holder are reduced. Furthermore, sample interactions in terms of infrared radiations are reduced.

In embodiments, the top surface of the sample holder has an infrared emissivity between 0.1 and 1, preferably of at least 0.8. This advantageously reduces disturbing reflections such that potential artefacts due to such reflections captured by the imaging device are limited.

In embodiments, a width of the sample wells of the sample holder is 1 to 100 times greater than a thermal diffusion length of the magnetic nanoparticle sample. It is preferred that the width of the sample wells of the sample holder is at least 10 times greater than a thermal diffusion length of the magnetic nanoparticle sample. If the width of the sample wells of the sample holder is substantially greater than a thermal diffusion length of the magnetic nanoparticle sample, the sample can be considered as an extended heat source. This configuration is optimal for the calculation of the SAR using amplitude image and/or values.

A second aspect of the invention relates to a lock-in thermography system for examining thermal radiation signals of magnetic nanoparticle samples and comprising a sample holder according to the first aspect of the invention. The lock-in thermography system further comprises:
   a coil surrounding at least partially the sample holder,
   a generator for generating an alternating magnetic field by means of the coil,
   a thermal imaging device for detecting a thermal radiation of at least one of the magnetic nanoparticle samples arranged in the sample holder, wherein the thermal radiation is a result of the alternating magnetic field, and
   an image processing device connected to the thermal imaging device, for capturing and processing images generated by said thermal imaging device.

In a third aspect of the invention the objective is solved by a method for examining thermal radiation signals of magnetic nanoparticle samples by means of a lock-in thermography system according to the second aspect of the invention.

At least a magnetic nanoparticle sample is arranged in a sample well of the sample holder of the lock-in thermography system. The following steps depend on the type of imaging device used in the lock-in thermography system.

If the thermal imaging device comprises an infrared camera with an optical lens, the following steps are carried out for the at least one magnetic nanoparticle:
   applying an amplitude-modulated or frequency-modulated alternating magnetic field at a predefined frequency for a predefined number of cycles by means of the generator,
   recording images of thermal radiation of the sample holder containing at least one magnetic nanoparticle sample for at least a part of the number of cycles by means of the thermal imaging device,
   demodulating the images of thermal radiation by means of the image processing device,
   calculating an amplitude image and optionally calculating a phase image,
   deriving a specific absorption rate of said at least one magnetic nanoparticle sample at least from the amplitude images, and
   deriving an intrinsic loss of power of said at least one magnetic nanoparticle sample from said specific absorption rate.

If the thermal imaging device comprises an array of infrared sensors with a corresponding array of lenses, the following steps are carried out for the at least one magnetic nanoparticle:

applying an amplitude-modulated or frequency-modulated alternating magnetic field at a predefined frequency for a predefined number of cycles by means of the generator, recording values of thermal radiation of the sample holder containing at least one magnetic nanoparticle sample for at least a part of the number of cycles by means of the thermal imaging device, demodulating the values of thermal radiation by means of the image processing device, calculating amplitude values and optionally calculating phase values, deriving a specific absorption rate of said at least one magnetic nanoparticle sample at least from the amplitude values, and deriving an intrinsic loss of power of said at least one magnetic nanoparticle sample from said specific absorption rate.

The lock-in thermography system and the method for examining thermal radiation signals of magnetic nanoparticle samples have the advantage of yielding very accurate results with respect to characterization of thermal behaviour of MNPs. As the system uses a sample holder according to the first aspect of the invention the influence of the sample holder material itself with respect to the distribution of thermal radiation of the sample or samples subjected to the AMF on the top surface of the sample holder is reduced.

Preferred applications of the lock-in thermography system according to the second aspect of the invention include examination of thermal radiation signals of superparamagnetic iron oxide nanoparticles embedded in a medium or a combination of mediums selected from one of: tissue, tissue phantoms, gels, suspensions, solid medium, by means of the method according to the third aspect of the invention.

BRIEF DESCRIPTION OF THE DRAWINGS

Embodiments, advantages and applications of the invention result from the dependent claims and from the now following description by means of the figures.

It is shown in.

In the drawings same references denote same or similarly acting components.

DETAILED DESCRIPTION OF THE INVENTION

It is noted that in the context of the present document the term "system" in connection with lock-in thermography refers to a device or installation.

Terms like "top" refer to a direction towards the thermal imaging device and terms like "bottom" away from the thermal imaging device.

The term "tissue phantom" is defined as a material with good tissue-mimicking properties which can be used for in-vitro studies in order to predict in-vivo effects.

For the purposes of this document the term "opaque" shall be understood within the usual tolerances of opacity implied in optics. For example, the degree of opacity of a filter blocking infrared radiation, e.g. as used in photography for filtering infrared light before reaching the CCD-sensor of a camera, is valid for the present description.

Figure 1:
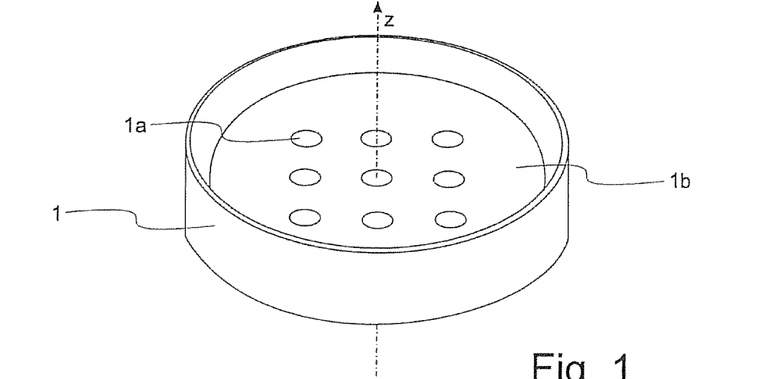
FIG. 1 a perspective view of an exemplary sample holder according to the first aspect of the invention.

FIG. 1 shows a perspective view of an exemplary sample holder 1 according to the first aspect of the invention. The sample holder 1 is adapted to hold samples of MNPs in sample wells 1a arranged of a sample holder top surface 1b. It is preferred that the sample holder 1 comprises an array of sample wells arranged in a structured way, e.g. in the way shown in FIG. 1. In this way it is possible to examine a plurality of samples at the same time. The only limitations for the number of sample wells 1a are given by the size of the lock-in thermography system using the sample holder 1 (particularly maximum image size which can be recorded with the infrared imaging device) and the first, second and third distances fulfilling the condition as stated in the first aspect of the invention.

The sample holder 1 of FIG. 1 is shown as circular sample holder 1. Other shapes may however also be used, e.g. the sample holder 1 could also have a square shape.

In operation, the sample holder 1 containing the sample or samples is placed inside an AMF. The amplitude of the AMF varies periodically with time at a specific frequency f. The sample temperature is monitored using an infrared imaging device. In order to extract from the temperature variations of the sample quantitative parameters like for example the specific absorption rate (SAR), which will be described later in the context of the lock-in thermography system according to the second aspect of the invention (FIGS. 4 and 5), the present invention is based on the finding that not only the known factors dealt with in existing solutions, e.g. imaging system, electromagnetic excitation of the samples, software algorithms, are important parameters for reaching precise results, but that dimensions of the sample holder itself plays an important role and should be carefully selected. This will be described in more detail in the context of FIG. 2.

The material of the sample holder 1 also has an effect on measurements. Preferably, the material of the sample holder is plastic or polymer, which are opaque to infrared thermal radiation. In preferred embodiments it is chosen from a group consisting of polyethylene HD, polyethylene SD, polystyrene, and polypropylene.

The table below gives an example of calculating the thermal diffusion length $\lambda_1$ for different potential sample holder materials for frequency f of 0.5 Hz.

| Material<br>Units | $\rho$<br>[kg/m$^3$] | c<br>[kJ/kg/° C.] | k<br>[W/m/° C.] | $\lambda_1$ [mm]<br>@ 0.5 Hz |
|---|---|---|---|---|
| $(C_2H_4)_n$ Polyethylene HD | 0.980 | 1.8 | 0.50 | 0.42 |
| $C_2H_4)_n$ Polyethylene LD | 0.920 | 2.2 | 0.33 | 0.32 |
| $(C_8H_8)_n$ Polystyrene | 1.050 | 1.3 | 0.16 | 0.27 |
| $(C_3H_6)_n$ Polypropylene | 0.910 | 1.8 | 0.22 | 0.29 |

As mentioned, it is preferred that the top surface 1b of the sample holder 1 has an infrared emissivity between 0.1 and 1, preferably of at least 0.8. Depending on the choice of the material for the sample holder 1, it is also conceivable that the top surface 1b of the sample holder 1 is treated in order to improve infrared emissivity. For example, the top surface 1b can be coated with a material fulfilling the above infrared emissivity requirements.

Figure 2:
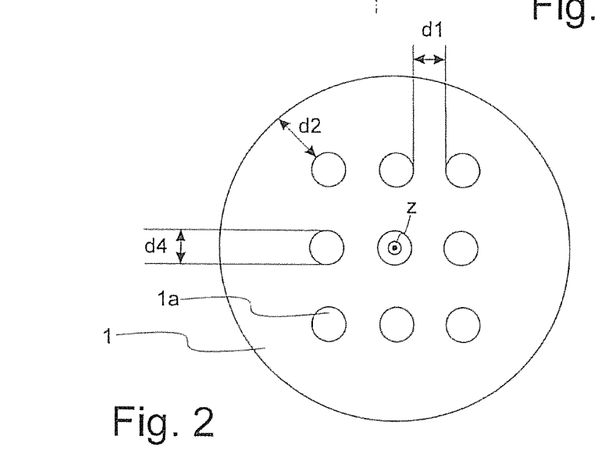
FIG. 2 a top view of the sample holder of FIG. 1.
Figure 3:
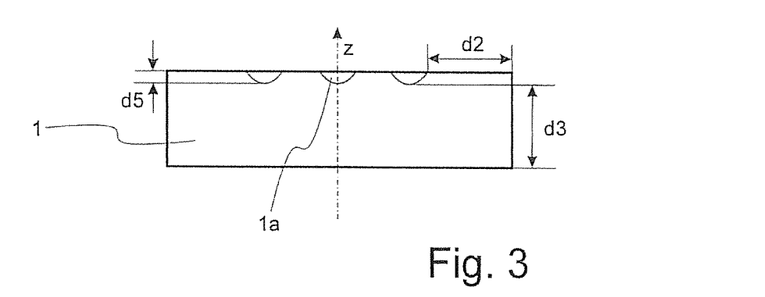
FIG. 3 a side view of the sample holder of FIG. 1.

FIG. 2 shows a top view and FIG. 3 a side view of the sample holder of FIG. 1.

A first distance d1 denotes the distance between neighboring sample wells 1a. For simplification reasons it is preferred that all sample wells 1a are arranged at the same distance with respect to adjacent sample wells.

A second distance d2 denotes the distance between each peripheral sample well 1a and a respective edge of the top surface 1b of the sample holder 1. The second distance d2 shall be understood as the shortest distance to said edge. In the present example of a circular sample holder 1 the second distance d2 is regarded as the shortest length of a line starting at the edge of a peripheral sample well 1a and being perpendicular on a tangent on the edge of the sample holder 1. If the sample holder 1 would be square, the second distance d2 would correspond to the length of a line perpendicular on the side of the square facing the respective peripheral sample well.

A third distance d3 denotes the distance between a deepest point of the sample wells 1a and a bottom of the sample holder 1.

Regarding the first aspect of the invention each one of the first and/or the second and/or the third distances d1-d3 shall be much larger than a thermal diffusion length λ1 of the sample holder material. As mentioned, an improvement of measurement accuracy for pre-characterization of MNPs can be reached if at least one of said distances or a combination of at least two of said distances is chosen to fulfil said criterion.

It is noted that the sample should be considered as an "extended heat source". The term "extended heat source" is known in the field of lock-in thermography and is e.g. described in the book "Lock-in thermography, Basics and Use for Functional Diagnostics of Electronic Components" by O. Breitenstein and M. Langenkamp. On the one hand it is preferred that a width d4 of the sample wells is preferably at least 10 times greater than the thermal diffusion length λ2 of the magnetic nanoparticle sample, as already mentioned. The thermal diffusion length λ2 of the sample in [mm] is defined as:

$$\lambda 2 = \sqrt{\frac{2k}{2\pi \rho c f}}$$

where k is the sample thermal conductivity in [W/m/° C.], ρ is the sample density in [kg/m$^3$], c is the sample heat capacity in [kJ/kg/° C.], and f is frequency at which the amplitude of the AMF is modulated in [Hz]. The following table shows an example of the above parameters in case the sample is pure water at 20° C.

| Material [Units] | ρ [kg/m$^3$] | c [kJ/kg/° C.] | k [W/m/° C.] |
|---|---|---|---|
| H$_2$O @ 20° C. | 0.998 | 4.1 | 0.60 |

If the frequency of the magnetic field is modulated at a frequency of 0.5 Hz, λ2 will equal 0.30 mm. According to the above condition, the dimensions of the sample should consequently be at least 3 mm in order for the sample to be considered an extended heat source.

On the other hand, the sample dimensions should be small enough in comparison to spatial variations of the amplitude AMF in order to be able to homogeneously heat up the sample. In other words, if the sample holder dimensions are too high, the possibility that inhomogeneities of the AMF occur increases. The highest acceptable limit of the sample holder dimensions may vary strongly depending on the measurement setup, e.g. depending on the used coil (described below in connection with FIG. 4) and the used shape/material of the sample holder. For example, measurements with a coil by nanoTherics used in the Magnetherm® version 1.5 showed that the AMF varies as a continuum between the middle and the external sample wells (radius=1 cm). It can decrease up to 20% (i.e. middle is at 100% borders are at 80%) for this specific coil. Hence, the extent of AMF-variations may change for each coil model/number of turns. Consequently, the acceptable limit is best derived by trials with the equipment available for the respective measurement setup.

Consequently, the two criteria discussed above give a lower and an upper boundary for the sample (MNP) dimensions.

It is understood that the sample well dimensions are adapted such that they can receive a sample (medium containing MNPs). The sample wells 1a are preferably round, having a maximum depth denoted with d5 in FIG. 2. This shape is preferred as manufacturing of the sample wells 1a can be accomplished very easy by drilling respective holes in the top surface 1b of the sample holder 1. However, it is clear that the sample wells 1a may also have other shapes.

Figure 4:
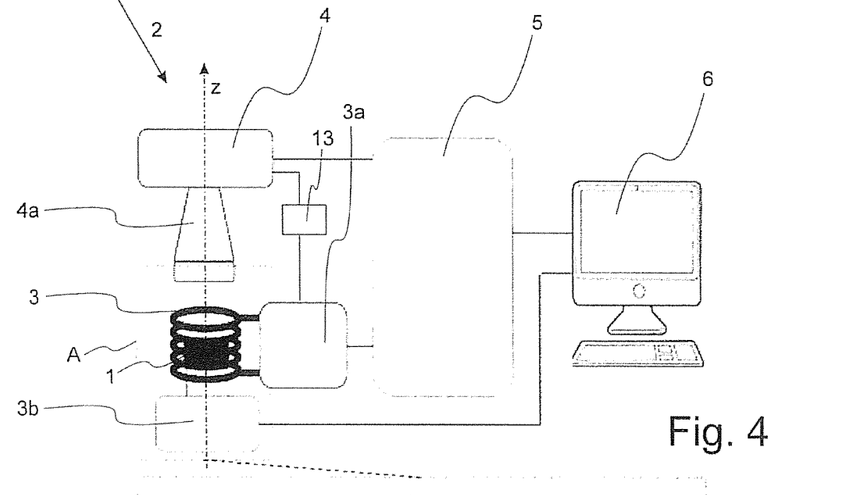
FIG. 4 a schematized view of an exemplary lock-in thermography system according to the second aspect of the invention.
Figure 5:
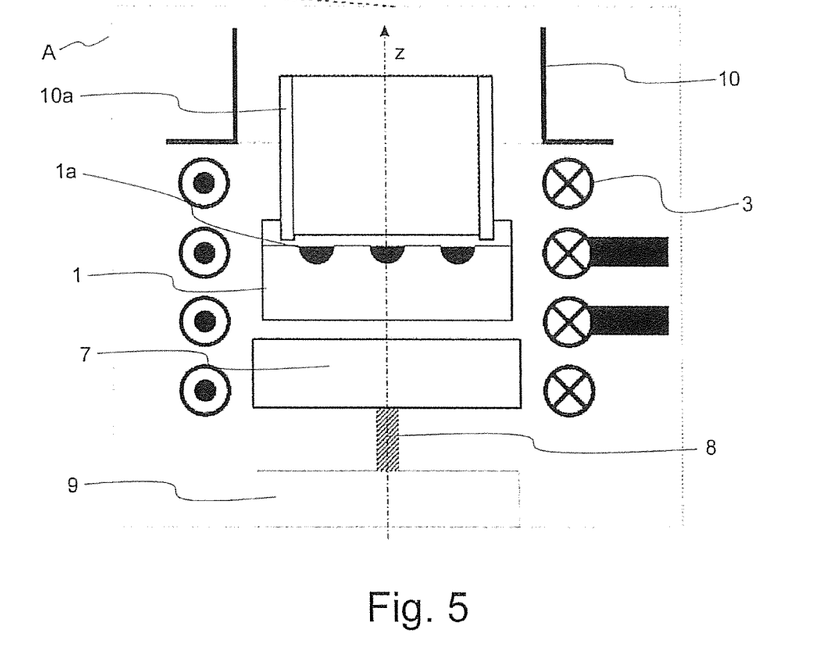
FIG. 5 a schematized view of a detail of FIG. 4.

FIG. 4 shows a schematized view of an exemplary lock-in thermography system 2 according to the second aspect of the invention and FIG. 5 a schematized view of detail A of FIG. 4. The lock-in thermography system 2 comprises a sample holder 1 according to the first aspect of the invention.

A coil 3 surrounds at least partially the sample holder 1. The coil is an ordinary coil, e.g. a coil manufactured by the company nanoTherics, Newcastle under Lyme, United Kingdom. This company is also a manufacturer of magnetic nanoparticles and provides systems for generating AMFs.

The coil 3 is connected to a generator 3a for generating an alternating magnetic field (AMF). Magnetic field parameters and suitable generators 3a are known in the field of lock-in thermography and will therefore not be described here in detail. The AMF heats up the sample or samples arranged in the sample holder 1 in order to achieve a thermal radiation of the samples.

The lock-in thermography system 2 further comprises a thermal imaging device 4 for detecting a thermal radiation of at least one of the magnetic nanoparticle samples arranged in the sample holder 1. The thermal imaging device will be described in more details in connection with FIGS. 6 and 7.

Furthermore, an image processing device 6 is provided, which is connected to the thermal imaging device 4 for capturing and processing images generated by said thermal imaging device 4. In embodiments like the exemplary embodiment of FIG. 4 an analog/digital converter 5 may be used as an interface between the thermal imaging device 4 and the image processing device 6 as well as between the generator 3a and the image processing device 6, if necessary.

The image processing device is preferably a computer 6 with display means for visualizing measurement results, i.e. the recorded thermal distribution of the sample holder top surface 1b. Certainly, dedicated hardware solutions for automatic processing of the incoming image data can also be used, however a computed is preferred, as it may also serve for controlling other parameters of the lock-in thermography system 2.

A sample holder support 3b is provided for attaching the sample holder 1. The sample holder support 3b is preferably a simple support having a plate for fixing the sample holder 1 inside the coil 3. In other embodiments sample holder support may comprise multiple elements which are best seen in FIG. 5. In this embodiment the sample holder 1 is mounted on a supporting plate 7 which is connected to an actuator 9 via an adjustment shaft 8. This setup may be used if it is desired that the height of the sample holder 1, particularly the height of sample holder top surface 1b, is adjustable. The actuator 9 may be controlled by the computer 6 mentioned above. Even though this alternative can be used in the lock-in thermography system 2, normally the simple support is used due to lower costs, as adjustment of the setup in view of focusing of the thermal imaging device 4 is in most cases either obsolete due to an initial fixed positioning of the thermal imaging system or it can be carried out by adjusting optics of the imaging device 4.

It is preferred that the space between the sample holder top surface 1b and the thermal imaging device 4 as well as the coil 3 is insulated from radiation originating from the environment by an insulation 10 in order to avoid as much as possible thermal influences from outside which would otherwise falsify the measurement results. In other words, quasi-adiabatic conditions can be assumed for the measurement setup, with negligible tolerance. Optionally, it is also possible to implement a second insulation for insulating the magnetic nanoparticle samples arranged in the sample holder from heat radiated by the coil. However, this type of insulation is normally not required.

In embodiments it is possible to optionally use a synchronization device 13 for synchronizing the generator 3a with the thermal imaging device 4.

In the following the thermal imaging device 4 is described in more detail by means of the two exemplary embodiments depicted in FIGS. 6 and 7.

Figure 6:
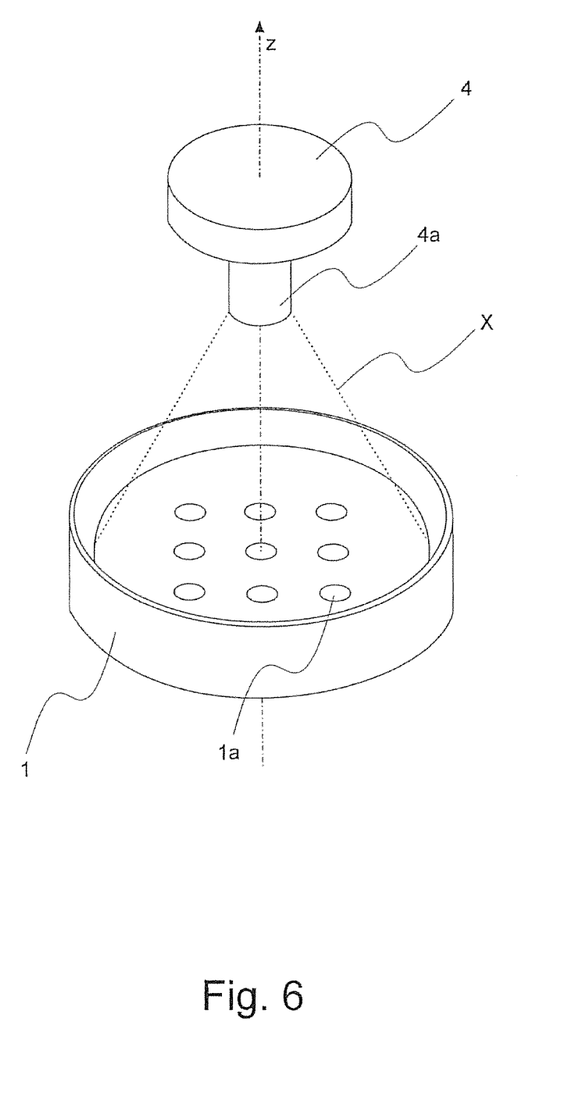
FIG. 6 a schematized perspective view of a first embodiment of an imaging device of the lock-in thermography system of FIG. 4.

FIG. 6 shows a schematized perspective view of a first embodiment of an imaging device 4 of the lock-in thermography system 2 of FIG. 4. In this embodiment an infrared camera 4 with an optical lens 4a is used as imaging device. This embodiment was also exemplarily used for in FIG. 4. The lens 4a is adjusted in such a way that its focus is on the top surface 1b of the sample holder 1. The camera system 4 with the lens 4a are arranged at such a distance from the top surface 1b of the sample holder 1 that at least the entire area of the top surface 1b containing the sample wells 1a, preferably the entire top surface 1b, is visible. This is illustrated by lines X in FIG. 6.

Figure 7:
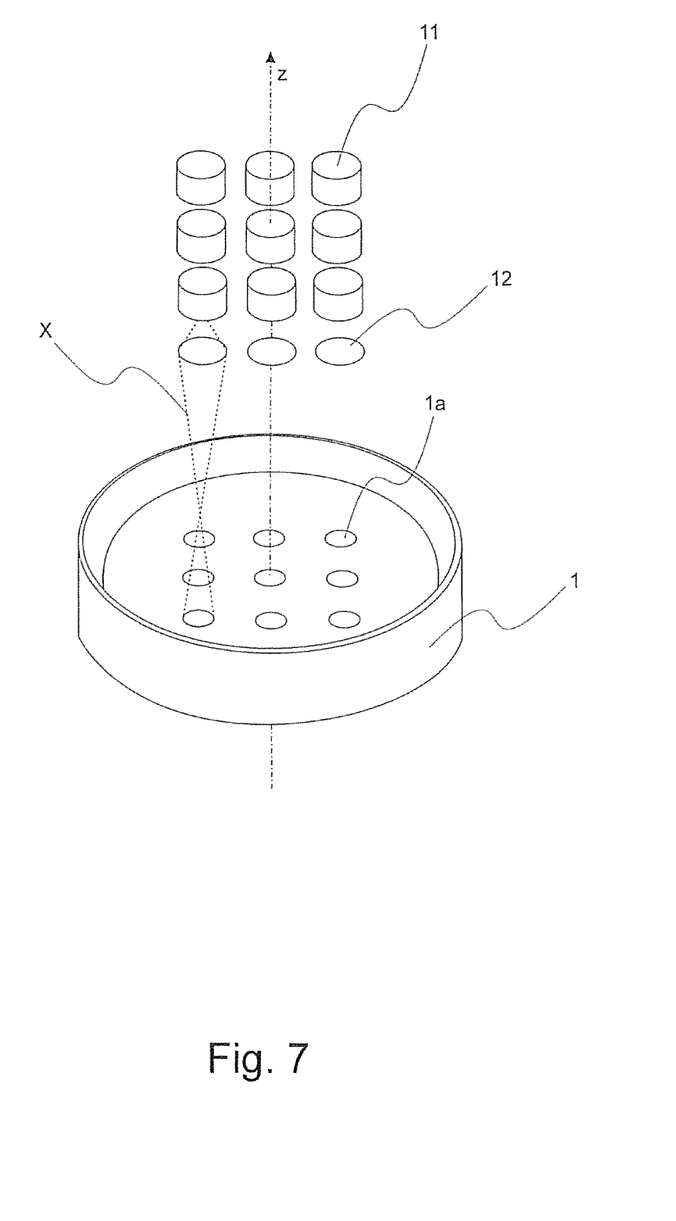
FIG. 7 a schematized perspective view of a second embodiment of an imaging device of the lock-in thermography system of FIG. 4.

FIG. 7 shows a schematized perspective view of a second embodiment of an imaging device of the lock-in thermography system 2. In this embodiment the thermal imaging device comprises an array of infrared sensors 11 with a corresponding array of lenses 12 which are preferably plastic lenses. A focus of the lenses 12 is adjustable such that the entire top surface 1b of the sample holder 1 is focused on the thermal imaging device 11. In the figure it is shown exemplarily by the lines X for one sensor 11 how the corresponding lens 12 is used for projecting the image of one sample well 1a onto the infrared sensor 11 to which it is attributed. In embodiments, the lenses 12 are adjustable with respect to height, such that the imaging device 11 can be used with sample wells 1a of different sizes.

In the following a workflow of a method according to the third aspect of the invention for examining thermal radiation signals of magnetic nanoparticle samples by means of the lock-in thermography system 2 according to FIG. 4 is described by means of FIG. 8, which shows a diagram illustrating the method comprising the steps described in the following.

In a first general step 101, which is the same for both imaging devices (FIGS. 6 and 7) and is considered a preparatory step, the at least one magnetic nanoparticle sample is arranged in a sample well 1a of the sample holder 1.

Generally, the method has two variations, depending on the type of thermal imaging device used. Therefore, for the sake of completeness another preparatory step 102 is named here, consisting in determining which type of imaging device is used in the lock-in thermography system 2.

If the thermal imaging device is an infrared camera 4 with an optical lens 4a according to FIG. 6, the left branch of the flowchart is followed, which comprises the steps set forth below.

The thermal imaging device is focused on the top surface 1b of the sample holder 1 at step 111. This is another preparatory step named for the sake of completeness and also not considered part of the actual MNP examination process.

Subsequently, at step 103, an amplitude-modulated or frequency-modulated alternating magnetic field (AMF) is applied at a predefined frequency for a predefined number of cycles by means of the generator 3a. The AMF is preferably a periodic amplitude-modulated or a frequency-modulated AMF. In embodiments, the AMF has a square or a harmonic waveform. The invention is however not limited to these types of AMF.

Thereafter, images of thermal radiation of the sample holder 1 (i.e. top surface 1b of the sample holder) containing at least one magnetic nanoparticle sample are recorded for at least a part of the number of cycles by means of the thermal imaging device 4 at step 112.

Then, the images of thermal radiation are demodulated by means of the image processing device 6 at step 104. In this context it is noted that the demodulation step does not necessarily require synchronization of the thermal imaging device 4 with the generator 3a, such that the synchronization device 13 of FIG. 4 doesn't have to be used.

Subsequently, an amplitude image is calculated at step 113. Optionally, a phase image and phase values may also be calculated at this step.

Depending on the setup of the thermal imaging device 4 with respect to the total surface of the top surface 1b of the sample holder 1 which can be captured by the camera 4, an additional step 114 of extracting at least a region of interest (ROI) corresponding to a position of the at least one magnetic nanoparticle sample is carried out after step 113 of calculating the amplitude image. This step is particularly useful when the sample holder 1 only holds MNP-samples in some of the sample wells 1a. In this case it is not necessary to perform calculations for the entire top surface 1b but only the interesting regions can be extracted in order to simplify and accelerate computation.

A further optional step 115 of calculating an average amplitude value from all amplitude images may be carried out for at least one region of interest of the sample holder surface 1b after the step 114 of extracting at least a region of interest.

Subsequently, a step 105 of correcting the amplitude values is carried out, which be explained in more detail later.

Thereafter, at step 106, a specific absorption rate (SAR) of said at least one magnetic nanoparticle sample is derived at least from the amplitude images. If desired, also the phase image and phase values optionally calculated at step 113 may be included for deriving the SAR, particularly if initial non-steady temperature phases, i.e. a thermal relaxation time, shall be taken into account.

Finally, an intrinsic loss of power (ILP) of said at least one magnetic nanoparticle sample is derived from said specific absorption rate at step 107.

If the thermal imaging device comprises an array of infrared sensors 11 with a corresponding array of lenses 12, the following procedure is used.

After the step 101 a step of adjusting a focus of the lenses 12 such that the entire top surface 1b of the sample holder 1 is focused on the thermal imaging device 11, 12 is carried out. This is a preparatory step named for the sake of completeness and also not considered part of the actual MNP examination process.

Like for the first variant with a camera 4, the step 103 of applying an amplitude-modulated or frequency-modulated alternating magnetic field at a predefined frequency for a predefined number of cycles by means of the generator 3a is carried out. As mentioned, the AMF is preferably a harmonic amplitude-modulated or a frequency-modulated AMF. In embodiments, the AMF has a square waveform. However, the invention is not limited to these types of AMFs.

Subsequently, values of thermal radiation of the sample holder 1 containing at least one magnetic nanoparticle sample are recorded at step 122 for at least a part of the number of cycles by means of the thermal imaging device 11, 12.

Then, like in the case of using a camera 4, the images are demodulated by means of the image processing device 6 at step 104.

Subsequently, amplitude values and optionally a phase image and phase values are calculated at step 123.

Thereafter, a step 105 of correcting the amplitude values is carried out, which be explained in more detail later.

Then the specific absorption rate (SAR) of said at least one magnetic nanoparticle sample is derived at least from the amplitude values at step 106. If desired, also the phase image and phase values optionally calculated at step 123 may be included for deriving the SAR.

Like for the variant using a camera 4 an intrinsic loss of power (ILP) of said at least one magnetic nanoparticle sample is derived from said specific absorption rate at step 107.

In the following the demodulation step 104, the step 105 of correcting the amplitude image or amplitude values, the SAR-calculation step 106 and the ILP-calculation step 107 will be described in more detail. The difference between the two options of thermal imaging device that in case of using a camera 4 thermal radiation images or amplitude images, respectively, are used, and in case of using sensors 11 thermal radiation values or amplitude values, respectively, are used, has no influence on the now following description of said steps.

a) Lock-in Demodulation (Step 104)

The transient infrared images (or the transient infrared values if using single thermal sensors), i.e. the thermal radiation images/values are processed according to the lock-in principle. Different realizations of this digital demodulation are possible (Breitenstein et al., 2010; Junyang et al., 2010; Krapez, 1998). In the present case the thermal signal measurement is achieved synchronously with the modulation of the alternating magnetic field. In addition, the modu-lation frequency is low (at least 10 times lower) as compared to the acquisition rate of the thermal imaging device. In these conditions, as stated by Breitenstein (Breitenstein et al., 2010; Gupta and Breitenstein, 2006), synchronous narrow two channels correlation is the optimal digital lock-in algorithm. This method is also called Standard Lock-In Method (SLIM). A direct advantage of SLIM is that the transient infrared images/values do not need to be stored in the computer 6 or in the thermal imaging device memory and the demodulation can be achieved in real time.

The result of SLIM is an "in-phase" and "in-quadrature" image (or "in-phase" values and "in-quadrature" values if using single thermal sensors), that can be used to compute an amplitude image and optionally a phase image (or amplitude values and phase values if using single thermal sensors). The amplitude image represents the temperature oscillation amplitudes and is proportional to the energy dissipated by the sample. The phase represents the phase shift between the modulation of the alternating magnetic field and the sample surface temperature (Breitenstein et al., 2010), i.e. the top surface 1b of the sample holder. It is noted that for reasons of simplification it is assumed throughout this document that the surface of the samples arranged in the sample wells 1a are substantially in the same plane as the top surface 1b of the sample holder 1.

SLIM works under the assumption that the measurement is performed under "quasi steady-state" conditions. In other words, the sample surface temperature oscillates with time around a steady mean temperature. In reality, at the beginning of the modulation, the sample temperature varies during an initial non-steady phase. This initial period or thermal relaxation time, which depends mainly on the heat transfer resistance between the sample and its environment, will induce a phase and amplitude shift in the demodulated signal. Theoretically, one should wait until the quasi-steady-state is reached before demodulating the thermal signal, but practically, depending on the modulation parameters, this can take several minutes. Different techniques have been proposed in the literature to solve this problem. The technique used here is the one introduced by Gupta & Breitenstein (Gupta and Breitenstein, 2006) where the in-phase and in-quadrature images (or values) are corrected by subtracting the demodulation of the non-steady state period. A direct advantage of this drift correction method is that the transient infrared images (or values) do not need to be stored in the computer 6 or thermal imaging device memory and the demodulation can be achieved in real time.

By using a customized demodulation algorithm, the initial heating slope can be derived directly without any post-processing steps (e.g. fitting), thus reducing uncertainties and subjectivity.

It is noted that the phase image and phase values, which can optionally be calculated when the amplitude image/values is/are calculated, may also be used as parameter in the calculation, beside the amplitude images, when deriving the specific absorption rate of the magnetic nanoparticle samples.

b) Correction of Amplitude Image/Values (Step 105+CF)

It is noted that the term amplitude image is used for the case of using a camera 4 and the term amplitude values is used in connection with the usage of sensors 11. This distinction between image and values is used for the case that the optional steps of ROI-extraction and average calculation (steps 114, 115) are not carried out. However, if said steps are carried out, which is preferred, the result before correction is also amplitude values, such that for this specific case there is no distinction between the camera-variant and the sensor-variant.

The procedure of correcting the amplitude image or amplitude values yields a correction coefficient and is performed before the step of deriving the specific absorption rate for the samples to be examined. In fact this procedure at step 105 sums up a sequence of sub-steps which are preferably carried out at the location depicted in FIG. 8, but which can alternatively also be carried out before the actual examination according to FIG. 8, as they involve, generally said, the generation of reference values with samples having a known behavior (known ILP) in order to account for system-based measurement deviations. In other words, this correction accounts for inhomogeneity of the AMF and has the goal of obtaining correction factors (denoted CF in FIG. 8) which can subsequently be used for correcting the amplitude values of step 115 or 123, respectively. Hence, if the correction coefficient is already known the step 105 can be omitted.

In a first sub-step reference samples are arranged in each sample well of the sample holder, analog to step 101. In other words, if the correction factor calculation is carried out during the examination of target samples, the sample holder containing the samples to be examined is swapped with a, preferably identical, sample holder containing the reference samples.

If the thermal imaging device comprises an infrared camera 4 with an optical lens 4*a*, the thermal imaging device is subsequently focused on the top surface 1*b* of the sample holder 1, if necessary. In the present workflow this step doesn't have to be performed as the camera system 4, 4*a* has already been adjusted for the samples to be examined.

Then step 103 of generating the AMF is executed for the reference samples and images of thermal radiation of the reference samples are recorded for at least a part of the number of cycles by means of the thermal imaging device, analog to step 112. This is followed by demodulation of the images of thermal radiation by means of the image processing device (see step 104).

Subsequently, a calibration amplitude image is calculated based on the images of thermal radiation.

Then the specific absorption rate for each one of the reference samples is derived from the amplitude values and the intrinsic loss of power of each one of the reference samples is derived from said specific absorption rate in the way already described for the samples to be examined.

After that the correction coefficient is derived as ratio between the intrinsic loss of power and the known target intrinsic loss of power value. The target ILP value is used to determine the intensity of the magnetic field Ho in the central sample well. Hence, an ILP value equaling the target ILP value is set for the central sample well. The ILP for each other sample well 1*a* is calculated using Ho as magnetic field intensity according to the already described formula for ILP-calculation. Then the correction coefficient is determined for each sample well as:

$$c = (\text{ILP value})/(\text{target ILP value})$$

Finally, the sub-step CF (see FIG. 8) is carried out, consisting in correcting the amplitude image resulting from examination of the target samples by normalization with the correction coefficient c calculated with the correction procedure. After that the SAR- and ILP-calculations are carried out for the MNPs to be examined in the way already described.

If the thermal imaging device comprises an array of infrared sensors 11 with a corresponding array of lenses 12, the procedure only varies with respect to the focusing step and in that values of thermal radiation and amplitude are used instead of images.

It is mentioned that the MNP samples to be examined, which are arranged in the corresponding sample holder do not need to be repositioned inside the lock-in thermography system 2, as the measurements of their thermal radiation profile has already been carried out and stored in the computer 6.

c) Derivation of SAR (Step 106)

As mentioned, if a thermal camera 4 is used, the result of the previous lock-in demodulation is an amplitude image. Then the regions of interest (ROIs) that correspond to the sample holder locations (one ROI for each sample holder 1) are optionally extracted. An averaged amplitude value (step 115) is calculated for each ROI.

If single thermal sensors 11 are used, the result of the previous lock-in demodulation is already an averaged amplitude value for each sample holder 1.

Subsequently, the SAR is extracted in the following way.

Case 1): Harmonic modulation of the alternating magnetic field (step 103)

For each sample holder 1 the SAR is calculated using the following formula:

$$SAR = \frac{4\pi f_{mod} CA}{m_{MNP}}$$

where $f_{mod}$ is the modulation frequency (in Hz) of the alternating magnetic field, C is the heat capacity of the sample (in J/K), A is the averaged amplitude value (in K), and $m_{MNP}$ the mass of nanoparticles (in g). The unit of the SAR is W/g and describes the energy amount converted into heat per time and mass.

Case 2): Square-wave modulation of the alternating magnetic field (step 103)

For each sample holder 1, the SAR is calculated using:

$$SAR = \frac{\pi^2 f_{mod} CA}{m_{MNP}}$$

d) Derivation of ILP (Step 107)

Finally, the ILP is calculated in the next step (step 107) with the following formula:

$$ILP = \frac{SAR}{fH^2}$$

where f is the frequency of the magnetic field (in kHz), H the amplitude of the alternating magnetic field (in kA/m), and the SAR is given in W/kg. The unit of the ILP is nHm²/kg.

Figure 8:
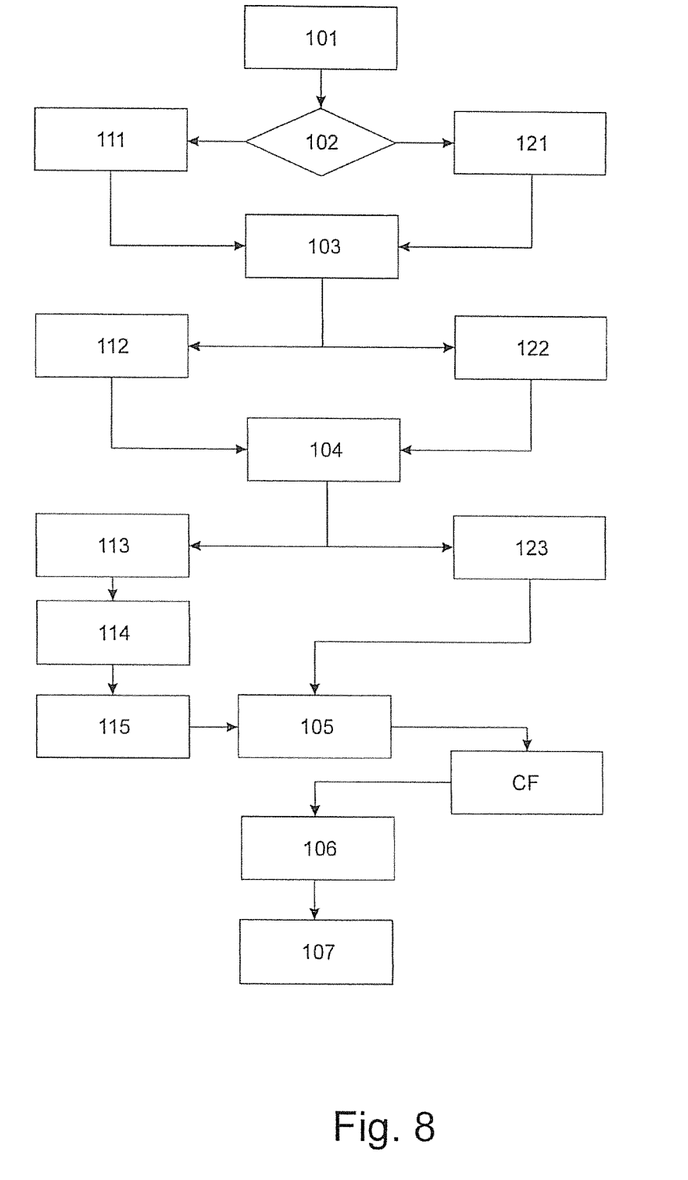
FIG. 8 a workflow of a method for examining thermal radiation signals of magnetic nanoparticle samples by means of a lock-in thermography system according to FIG. 4.

It is noted that FIG. 8 incorporates not only the necessary steps for examining the thermal radiation signals but also optional steps as described above in order to better illustrate the insertion of these steps. Hence, FIG. 8 is an exemplary embodiment of the method according to the third aspect of the invention and shall not be considered as a limitation thereto.

To summarize, the present invention uses lock-in thermography (LIT) for therapeutic magnetic hyperthermia and provides a standardized and accurate possibility of investigation of the respective nanoparticles. The hardware and software elements of the invention, particularly the customized sample holders make it possible to use LIT to examine and numerically quantify the thermal signatures/radiation of MNPs when exposed to an AMF. Compared to results obtained by conventional methods (i.e. fiberoptic cables or standard thermography) and simulations, the current approach described herein improves precision of such qualification and/or quantification of nanoparticles. Finally, we demonstrate that the method is universal to samples in any state (i.e., liquid, semi-solid or aggregated), because large surface areas can be probed without contact to the sample.

While there are shown and described presently preferred embodiments of the invention, it is to be distinctly understood that the invention is not limited thereto but may otherwise variously be embodied and practised within the scope of the following claims. Accordingly, terms like "preferred" or "in particular" or "particularly" or "advantageously", etc. signify optional and exemplary embodiments only.

REFERENCE LIST

1=sample holder
1a=sample well
1b=sample holder top surface
2=lock-in thermography system
3=coil
3a=coil supply/function generator
3b=sample holder support
4=imaging device
4a=lens
5=analog/digital converter
6=computer
7=supporting plate for sample holder
8=adjustment shaft for supporting plate
9=actuator for adjustment shaft
10=insulation
11=infrared sensor
12=infrared sensor lens
13=synchronization device
A=detail
X=lens image
d1=distance between adjacent sample wells in a row
d2=distance between adjacent sample wells
d3=minimum thickness of sample holder
d4=diameter of sample well
d5=maximum depth of sample well

The invention claimed is:

1. A sample holder for holding a plurality of magnetic nanoparticle samples and for usage in a lock-in thermography system, comprising: a plurality of sample wells distributed on a top surface of the sample holder, wherein each of the sample wells is adapted to hold a magnetic nanoparticle sample consisting of a plurality of magnetic nanoparticles embedded in a medium, wherein the sample wells are distributed on the top surface such that a first distance between neighboring samples wells and a second distance between each peripheral sample well and a respective edge of the top surface of the sample holder and a third distance between a deepest point of the sample wells and a bottom of the sample holder is at least 10 times greater, than a thermal diffusion length of the sample holder material, and wherein the thermal diffusion length is $$\lambda 2 = \sqrt{\frac{2k}{2\pi \rho c f}}$$

where k is the sample thermal conductivity in [W/m/° C.], p is the sample density in [kg/m³], c is the sample heat capacity in [kJ/kg/° C.], and f is frequency at which the amplitude of the AMF is modulated in [Hz].

2. The sample holder according to claim 1, wherein a width of the sample wells is 1 to 100 times greater than a thermal diffusion length of the magnetic nanoparticle sample.

3. The sample holder according to claim 1, wherein the first distance and the second distance and the third distance are equal.

4. The sample holder according to claim 1, wherein the material of the sample holder is plastic or polymer, chosen from a group consisting of polyethylene HD, polyethylene SD, polystyrene, and polypropylene.

5. The sample holder according to claim 1, wherein the sample holder consists of a sample holder material which is opaque to infrared thermal radiation.

6. The sample holder according to claim 1, wherein the top surface of the sample holder has an infrared emissivity between 0.1 and 1.

7. A lock-in thermography system for examining thermal radiation signals of magnetic nanoparticle samples, comprising a sample holder for holding a plurality of magnetic nanoparticle samples and for usage in a lock-in thermography system, comprising: a plurality of sample wells distributed on a top surface of the sample holder, wherein each of the sample wells is adapted to hold a magnetic nanoparticle sample consisting of a plurality of magnetic nanoparticles embedded in a medium, wherein the sample wells are distributed on the top surface such that a first distance between neighboring samples wells and/or a second distance between each peripheral sample well and a respective edge of the top surface of the sample holder and/or a third distance between a deepest point of the sample wells and a bottom of the sample holder is between 1 and 100 times greater, than a thermal diffusion length of the sample holder material, and wherein the thermal diffusion length is $$\lambda 2 = \sqrt{\frac{2k}{2\pi \rho c f}}$$

where k is the sample thermal conductivity in [W/m/° C.], p is the sample density in [kg/m³], c is the sample heat capacity in [kJ/kg/° C.], and f is frequency at which the amplitude of the AMF is modulated in [Hz] and further comprising:
a coil surrounding at least partially the sample holder,
a generator for generating an alternating magnetic field by the coil,
a thermal imaging device for detecting a thermal radiation of at least one of the magnetic nanoparticle samples arranged in the sample holder, wherein the thermal radiation is a result of the alternating magnetic field,
an image processing device connected to the thermal imaging device, for capturing and processing images generated by said thermal imaging device.

8. The lock-in thermography system according to claim 7, wherein the thermal imaging device comprises either an infrared camera with an optical lens focused on the top surface of the sample holder or comprises an array of infrared sensors with a corresponding array of lenses, particularly plastic lenses, wherein a focus of the lenses is adjustable such that the entire top surface of the sample holder is focused on the thermal imaging device.

9. The lock-in thermography system according to claim 7, wherein an insulation element for insulating the magnetic nanoparticle samples arranged in the sample holder from thermal radiation originating from the coil and/or the environment is provided around at least a part of the sample holder.

10. A method for examining thermal radiation signals of magnetic nanoparticle samples by a lock-in thermography system according to claim 7, wherein at least a magnetic nanoparticle sample is arranged in a sample well of the sample holder of the lock-in thermography system, comprising the steps of:
applying an amplitude-modulated or frequency-modulated alternating magnetic field at a predefined frequency for a predefined number of cycles by the generator, and,
if the thermal imaging device comprises an infrared camera with an optical lens,
recording images of thermal radiation of the sample holder containing at least one magnetic nanoparticle sample for at least a part of the number of cycles by the thermal imaging device,
demodulating the images of thermal radiation by the image processing device,
calculating an amplitude image and optionally calculating a phase image,
deriving a specific absorption rate of said at least one magnetic nanoparticle sample at least from the amplitude images, and
deriving an intrinsic loss of power of said at least one magnetic nanoparticle sample from said specific absorption rate,
or, if the thermal imaging device comprises an array of infrared sensors with a corresponding array of lenses,
recording values of thermal radiation of the sample holder containing at least one magnetic nanoparticle sample for at least a part of the number of cycles by the thermal imaging device,
demodulating the values of thermal radiation by the image processing device,
calculating amplitude values and optionally calculating phase values,
deriving a specific absorption rate of said at least one magnetic nanoparticle sample at least from the amplitude values, and
deriving an intrinsic loss of power of said at least one magnetic nanoparticle sample from said specific absorption rate.

11. The method according to claim 10, wherein a procedure of correcting the amplitude image or amplitude values is performed between the step of calculating an amplitude image or amplitude values and the step of deriving a specific absorption rate by carrying out the sub-steps of
swapping the sample holder containing the nanoparticle samples to be examined with a sample holder containing reference samples with a known target intrinsic loss of power value,
applying an amplitude-modulated or a frequency-modulated alternating magnetic field at a predefined frequency for a predefined number of cycles by the generator,
recording images of thermal radiation of the reference samples for at least a part of the number of cycles by the thermal imaging device,
demodulating the values of thermal radiation by the image processing device, and,
if the thermal imaging device comprises an infrared camera with an optical lens,
calculating a calibration amplitude image,
deriving a specific absorption rate for each one of the reference samples from the amplitude values,
deriving an intrinsic loss of power of each one of the reference samples from said specific absorption rate,
deriving a correction coefficient (c) as ratio between the intrinsic loss of power and the intrinsic loss of power target value, and
correcting the amplitude image or the amplitude values at least by normalization with the correction coefficient (c),
or, if the thermal imaging device comprises an array of infrared sensors with a corresponding array of lenses,
calculating calibration amplitude values,
deriving a specific absorption rate for each one of the reference samples from the amplitude values,
deriving an intrinsic loss of power of each one of the reference samples from said specific absorption rate,
deriving a correction coefficient (c) as ratio between the intrinsic loss of power and the intrinsic loss of power target value, and
correcting the amplitude image or amplitude values normalization with the correction coefficient (c).

12. The method according to claim 10, wherein a periodic amplitude-modulated or frequency-modulated alternating magnetic field is applied by the generator.

13. The method according to claim 10, wherein, if the thermal imaging device including an infrared camera with an optical lens, an additional step of extracting at least a region of interest (ROI) corresponding to a position of the at least one magnetic nanoparticle sample is carried out between the step of calculating the amplitude image and the step of deriving the specific absorption rate.

14. The method according to claim 13, wherein, if the thermal imaging device includes an infrared camera with an optical lens, a step of calculating an average amplitude value from all amplitude images is carried out for at least one of the regions of interest (ROI) of the sample holder top surface after the step of extracting at least a region of interest (ROI).

15. A method for using the lock-in thermography system according to claim 7, comprising the step of: examining thermal radiation signals of superparamagnetic iron oxide nanoparticles embedded in a medium or a combination of mediums selected from one of: tissue, tissue phantoms, gels, suspensions, solid medium, by applying an amplitude-modulated or frequency-modulated alternating magnetic field at a predefined frequency for a predefined number of cycles by the generator, and,
if the thermal imaging device comprises an infrared camera with an optical lens,
recording images of thermal radiation of the sample holder containing at least one magnetic nanoparticle sample for at least a part of the number of cycles by the thermal imaging device,
demodulating the images of thermal radiation by the image processing device,
calculating an amplitude image and optionally calculating a phase image, deriving a specific absorption rate of said at least one magnetic nanoparticle sample at least from the amplitude images, and deriving an intrinsic loss of power of said at least one magnetic nanoparticle sample from said specific absorption rate, or, if the thermal imaging device comprises an array of infrared sensors with a corresponding array of lenses, recording values of thermal radiation of the sample holder containing at least one magnetic nanoparticle sample for at least a part of the number of cycles by the thermal imaging device, demodulating the values of thermal radiation by the image processing device, calculating amplitude values and optionally calculating phase values, deriving a specific absorption rate of said at least one magnetic nanoparticle sample at least from the amplitude values, and deriving an intrinsic loss of power of said at least one magnetic nanoparticle sample from said specific absorption rate.

16. The sample holder according to claim 2, wherein the width of the sample wells is at least 10 times greater than the thermal diffusion length of the magnetic nanoparticle sample.

17. The sample holder according to claim 6, wherein the top surface of the sample holder has an infrared emissivity of at least 0.8.

18. The method according to claim 12, wherein an alternating magnetic field with a square or harmonic waveform is applied.

19. The sample holder according to claim 2, wherein the first distance and the second distance and the third distance are equal, wherein the material of the sample holder is plastic or polymer, chosen from a group consisting of polyethylene HD, polyethylene SD, polystyrene, and polypropylene, wherein the sample holder consists of a sample holder material which is opaque to infrared thermal radiation, and wherein the top surface of the sample holder has an infrared emissivity between 0.1 and 1.

20. The lock-in thermograph system according to claim 8, wherein an insulation element for insulating the magnetic nanoparticle samples arranged in the sample holder from thermal radiation originating from the coil and/or the environment is provided around at least a part of the sample holder.

* * * * *